(12) United States Patent
Malinowski et al.

(10) Patent No.: US 8,214,058 B2
(45) Date of Patent: *Jul. 3, 2012

(54) LEAD ASSEMBLIES WITH ONE OR MORE SWITCHING NETWORKS

(75) Inventors: Zdzislaw B. Malinowski, Castaic, CA (US); Salomo S. Murtonen, San Gabriel, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/902,340

(22) Filed: Oct. 12, 2010

(65) Prior Publication Data

US 2011/0029042 A1 Feb. 3, 2011

Related U.S. Application Data

(63) Continuation of application No. 11/654,806, filed on Jan. 17, 2007, now Pat. No. 7,835,803.

(60) Provisional application No. 60/759,528, filed on Jan. 17, 2006.

(51) Int. Cl.
*A61N 1/05* (2006.01)
(52) U.S. Cl. ........................................ 607/122; 607/119
(58) Field of Classification Search ............ 607/45, 607/55, 115, 117, 119, 122, 123, 137
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,627,850 A | 12/1986 | Deters et al. |
| 4,692,147 A | 9/1987 | Duggan |

(Continued)

FOREIGN PATENT DOCUMENTS

WO    WO 99/56818    11/1999

(Continued)

OTHER PUBLICATIONS

U.S. Appl. No. 11/654,806, filed Jan. 17, 2007; Office Communication mailed Apr. 8, 2009.

(Continued)

*Primary Examiner* — Carl H Layno
*Assistant Examiner* — Allen Porter, Jr.
(74) *Attorney, Agent, or Firm* — Frommer Lawrence & Haug LLP; Bruce E. Black

(57) ABSTRACT

Exemplary lead assemblies include a lead body having a plurality of conductor wires embedded therein, a plurality of electrode contacts at least partially disposed on an outer surface of the lead body, and a plurality of switching networks each configured to control an operation of one or more of the plurality of electrode contacts.

20 Claims, 12 Drawing Sheets

U.S. PATENT DOCUMENTS

| | | | |
|---|---|---|---|
| 4,725,852 A | 2/1988 | Gamblin et al. |
| 4,865,845 A | 9/1989 | Eckenhoff et al. |
| 4,961,434 A | 10/1990 | Stypulkowski |
| 5,000,194 A | 3/1991 | Van Den Honert et al. |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |
| 5,193,539 A | 3/1993 | Schulman et al. |
| 5,193,540 A | 3/1993 | Schulman et al. |
| 5,234,692 A | 8/1993 | Magruder et al. |
| 5,234,693 A | 8/1993 | Magruder et al. |
| 5,312,439 A | 5/1994 | Loeb |
| 5,417,719 A | 5/1995 | Hull et al. |
| 5,728,396 A | 3/1998 | Peery et al. |
| 6,038,480 A | 3/2000 | Hrdlicka et al. |
| 6,051,017 A | 4/2000 | Loeb et al. |
| 6,164,284 A | 12/2000 | Schulman et al. |
| 6,185,452 B1 | 2/2001 | Schulman et al. |
| 6,208,894 B1 | 3/2001 | Schulman et al. |
| 6,280,873 B1 | 8/2001 | Tsukamoto |
| 6,368,315 B1 | 4/2002 | Gillis et al. |
| 6,418,348 B1 | 7/2002 | Witte |
| 6,458,171 B1 | 10/2002 | Tsukamoto |
| 6,464,687 B1 | 10/2002 | Ishikawa et al. |
| 6,473,653 B1 | 10/2002 | Schallhorn et al. |
| 6,596,439 B1 | 7/2003 | Tsukamoto et al. |
| 6,605,383 B1 | 8/2003 | Wu |
| 6,607,843 B2 | 8/2003 | Ruth, II et al. |
| 6,826,430 B2 | 11/2004 | Faltys et al. |
| 2002/0111661 A1 | 8/2002 | Cross et al. |
| 2003/0083728 A1 | 5/2003 | Greatbatch et al. |
| 2003/0181966 A1 | 9/2003 | Morgan |
| 2003/0199930 A1 | 10/2003 | Grandjean |
| 2003/0199957 A1 | 10/2003 | Struble et al. |
| 2003/0204228 A1 | 10/2003 | Cross, Jr. et al. |
| 2003/0204232 A1 | 10/2003 | Sommer et al. |
| 2004/0102812 A1 | 5/2004 | Yonce et al. |
| 2005/0090885 A1 | 4/2005 | Harris et al. |

FOREIGN PATENT DOCUMENTS

| | | | |
|---|---|---|---|
| WO | WO 2005/042086 A1 | 5/2005 |

OTHER PUBLICATIONS

U.S. Appl. No. 11/654,806, filed Jan. 17, 2007; Office Communication mailed Sep. 23, 2009.

U.S. Appl. No. 11/654,806, filed Jan. 17, 2007; Office Communication mailed Jan. 21, 2010.

U.S. Appl. No. 11/654,806, filed Jan. 17, 2007; Notice of Allowance mailed Jul. 13, 2010.

FIG. 12

LEAD ASSEMBLIES WITH ONE OR MORE SWITCHING NETWORKS

RELATED APPLICATIONS

The present application claims priority under 35 U.S.C. §119(e) to U.S. Provisional Patent Application No. 60/759,528, by Zdzislaw Bernard Malinowski et al. filed on Jan. 17, 2006, and entitled "Addressable Electrode Array for Neurostimulation," and is a continuation of U.S. patent application Ser. No. 11/654,806 filed Jan. 17, 2007, now U.S. Pat. No. 7,835,803, the contents of which are hereby incorporated by reference in their entirety.

BACKGROUND

A wide variety of medical conditions and disorders have been successfully treated using implantable medical devices. Such implantable devices include, but are not limited to, stimulators or pulse generators, pacemakers, and defibrillators.

It is often desirable to electrically couple an implantable medical device to a lead having a plurality of electrodes disposed thereon so that the device may deliver electrical stimulation to a site within the body. A conventional lead includes a plurality of elongate conductors or wires covered by insulation. At a distal end of the lead, each conductor is connected to an exposed (i.e., non-insulated) electrode, or electrode contact. Each electrode contact is configured to provide an electrical interface with the tissue that is to be stimulated.

At a proximal end of a conventional lead, each conductor is connected to an exposed terminal contact. The exposed terminal contacts are configured to provide an electrical interface with the implantable device, or with a connector of an extension lead that connects with the implantable device. To this end, the implantable device may include a number of feedthroughs configured to facilitate electrical connection with each of the terminal contacts.

However, the number of electrodes that may be disposed on a conventional lead is often limited by the finite number of feedthroughs that may be included within the implantable device. Moreover, the number of electrodes that may be disposed on a conventional lead is limited by the number of wires that can be reliably and cost effectively fit and manufactured into the lead.

SUMMARY

Exemplary lead assemblies include a lead body having a plurality of conductor wires embedded therein, a plurality of electrode contacts at least partially disposed on an outer surface of the lead body, and a plurality of switching networks each configured to control an operation of one or more of the plurality of electrode contacts.

Methods of applying stimulation current to one or more stimulation sites include generating the electrical stimulation current, providing a lead body having a plurality of conductor wires embedded therein, providing a plurality of electrode contacts each having a corresponding switching network configured to control an operation thereof, and selectively applying the stimulation current to one or more stimulation sites via a subset of the electrode contacts by transmitting one or more stimulation parameters to one or more of the switching networks via one or more of the conductor wires.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 12 shows a ten-by-ten area within a patient that may be stimulated using a ten-by-ten array of electrode assemblies according to principles described herein.

Throughout the drawings, identical reference numbers designate similar, but not necessarily identical, elements.

DETAILED DESCRIPTION

Exemplary lead assemblies that minimize the number of conductor wires included therein are described heroin. In some examples, a lead assembly includes a plurality of electrode contacts at least partially disposed on an outer surface of a lead body. Each electrode contact is controlled by a corresponding switching network. In some examples, each conductor wire included within the lead assembly is electrically coupled to each switching network. In this manner, a single set of conductor wires may be used to transmit stimulation parameters to and/or otherwise control the operation of each electrode contact.

Methods of applying stimulation current to one or more stimulation sites include generating the electrical stimulation current, providing a lead body having a plurality of conductor wires embedded therein, providing a plurality of electrode contacts each having a corresponding switching network configured to control an operation thereof, and selectively applying the stimulation current to one or more stimulation sites via a subset of the electrode contacts by transmitting one or more stimulation parameters to one or more of the switching networks via one or more of the conductor wires.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

It will be recognized that the lead assemblies described herein may be used with any device configured to be electrically coupled thereto and are not limited to use with implantable stimulators only. For example, the lead assemblies described herein may be used with one or more devices configured to be located external to the patient. However, for illustrative purposes only, implantable stimulators will be used in the examples described herein.

Figure 1:
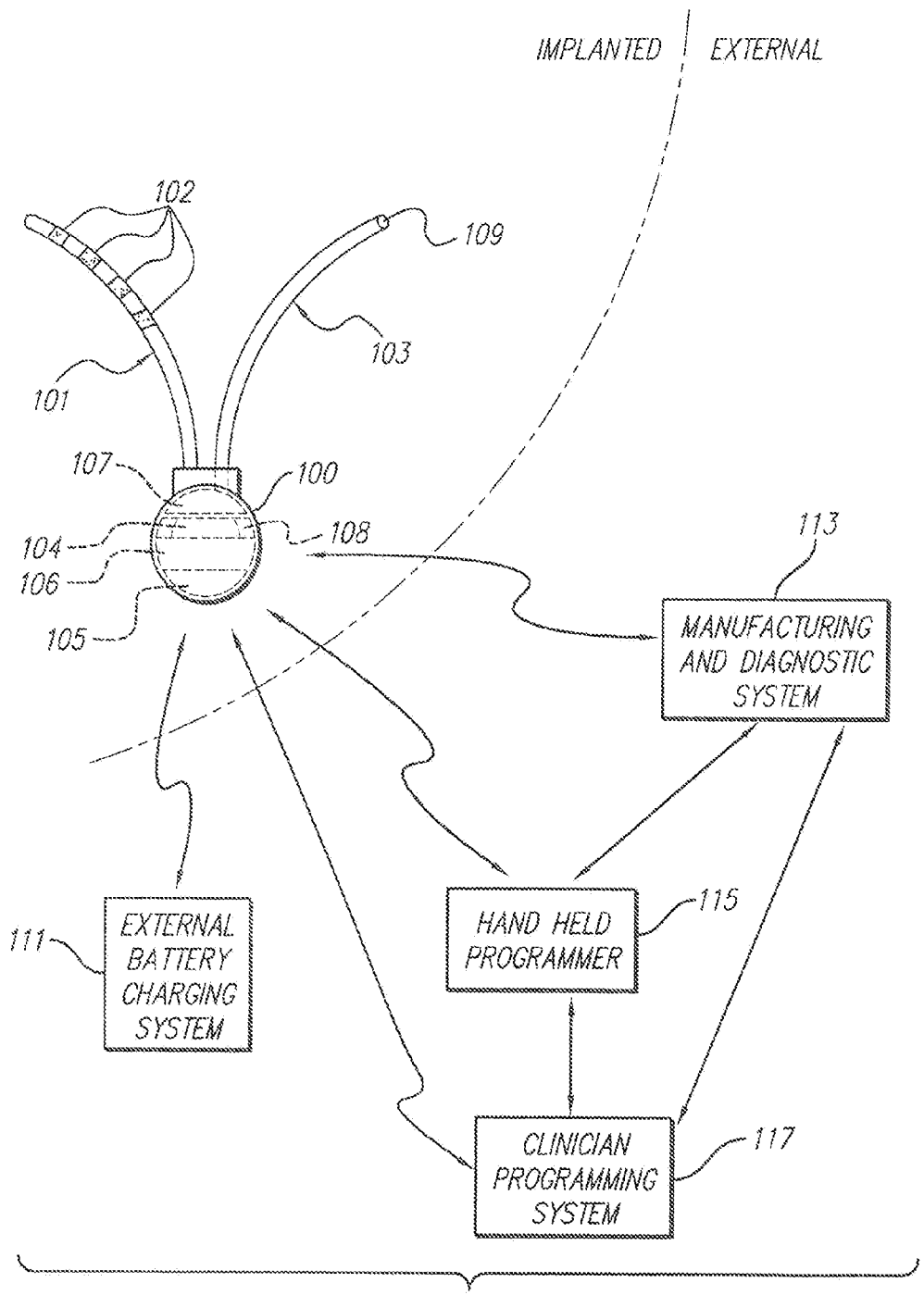
FIG. 1 illustrates an exemplary stimulator according to principles described herein.

To facilitate an understanding of an exemplary device with which the lead assemblies described herein may be used, an exemplary implantable stimulator will now be described in connection with FIG. 1. FIG. 1 illustrates an exemplary stimulator 100 that may be used to apply a stimulus to a stimulation site within a patient, e.g., an electrical stimulation of the stimulation site, an infusion of one or more drugs at the stimulation site, or both. The electrical stimulation function of the stimulator 100 will be described first, followed by an explanation of the possible drug delivery function of the stimulator 100. It will be understood, however, that the stimulator 100 may be configured to provide only electrical stimulation, only drug stimulation, both types of stimulation, or any other type of stimulation as best suits a particular patient.

The exemplary stimulator 100 shown in FIG. 1 is configured to provide electrical stimulation to one or more stimulation sites within a patient and may include a lead assembly 101 coupled thereto. In some examples, the lead assembly 101 includes an array of electrode assemblies 102 disposed thereon through which electrical stimulation current may be applied to a stimulation site. It will be recognized that the lead assembly 101 may include any number of electrode assemblies 102 arranged in any configuration as may serve a particular application. Moreover, it will be recognized that the electrode assemblies 102 described herein may perform any function as best serves a particular application such as, but not limited to, stimulating and/or sensing. The electrode assemblies 102 will be described in more detail below.

In some examples, as shown in FIG. 1, the lead assembly 101 is coupled directly to the stimulator 100. Alternatively, the lead assembly 101 and/or the stimulator 100 may include one or more connector assemblies and/or lead extension assemblies configured to facilitate coupling of the lead assembly 101 to the stimulator. The lead assembly 101 will be described in more detail below.

As illustrated in FIG. 1, the stimulator 100 includes a number of components. It will be recognized that the stimulator 100 may include additional and/or alternative components as best serves a particular application. A power source 105 is configured to output voltage used to supply the various components within the stimulator 100 with power and/or to generate the power used for electrical stimulation. The power source 105 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 105 may be recharged using an external charging system. One type of rechargeable power supply that may be used is described in U.S. Pat. No. 6,596,439, which is incorporated herein by reference in its entirety. Other battery construction techniques that may be used to make the power source 105 include those shown, e.g., in U.S. Pat. Nos. 6,280,873; 6,458,171; 6,605,383; and 6,607,843, all of which are incorporated herein by reference in their respective entireties.

The stimulator 100 may also include a coil 108 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 105.

For example, an external battery charging system (EBCS) 111 may be provided to generate power that is used to recharge the power source 105 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 100 via one or more communication links. It will be recognized that the communication links shown in FIG. 1 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 100. It will be recognized that any suitable communication link may be used among the various devices illustrated.

The external devices shown in FIG. 1 are merely illustrative of the many different external devices that may be used in connection with the stimulator 100. Furthermore, it will be recognized that the functions performed by any two or more of the external devices shown in FIG. 1 may be performed by a single external device.

The stimulator 100 may also include electrical circuitry 104 configured to generate the electrical stimulation current that is delivered to a stimulation site via one or more of the electrode assemblies 102. For example, the electrical circuitry 104 may include one or more processors, capacitors, integrated circuits, resistors, coils, and/or any other component configured to generate electrical stimulation current.

Additionally, the exemplary stimulator 100 shown in FIG. 1 may be configured to provide drug stimulation to a patient by applying one or more drugs at a stimulation site within the patient. To this end, a pump 107 may also be included within the stimulator 100. The pump 107 is configured to store and dispense one or more drugs, for example, through a catheter 103. The catheter 103 is coupled at a proximal end to the stimulator 100 and may have an infusion outlet 109 for infusing dosages of the one or more drugs at the stimulation site. In some embodiments, the stimulator 100 may include multiple catheters 103 and/or pumps 107 for storing and infusing dosages of the one or more drugs at the stimulation site.

The stimulator 100 may also include a programmable memory unit 106 configured to store one or more stimulation parameters. The stimulation parameters may include, but are not limited to, electrical stimulation parameters, drug stimulation parameters, and other types of stimulation parameters. The programmable memory unit 106 allows a patient, clinician, or other user of the stimulator 100 to adjust the stimulation parameters such that the stimulation applied by the stimulator 100 is safe and efficacious for treatment of a particular patient. The programmable memory unit 106 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

The stimulator 100 of FIG. 1 is illustrative of many types of stimulators that may be used to apply a stimulus to a stimulation site. For example, the stimulator 100 may include an implantable pulse generator (IPG) coupled to one or more leads having a number of electrodes, a spinal cord stimulator (SCS), a cochlear implant, a deep brain stimulator, a microstimulator, or any other type of implantable stimulator configured to deliver a stimulus at a stimulation site within a patient. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. Exemplary microstimulators suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 2:
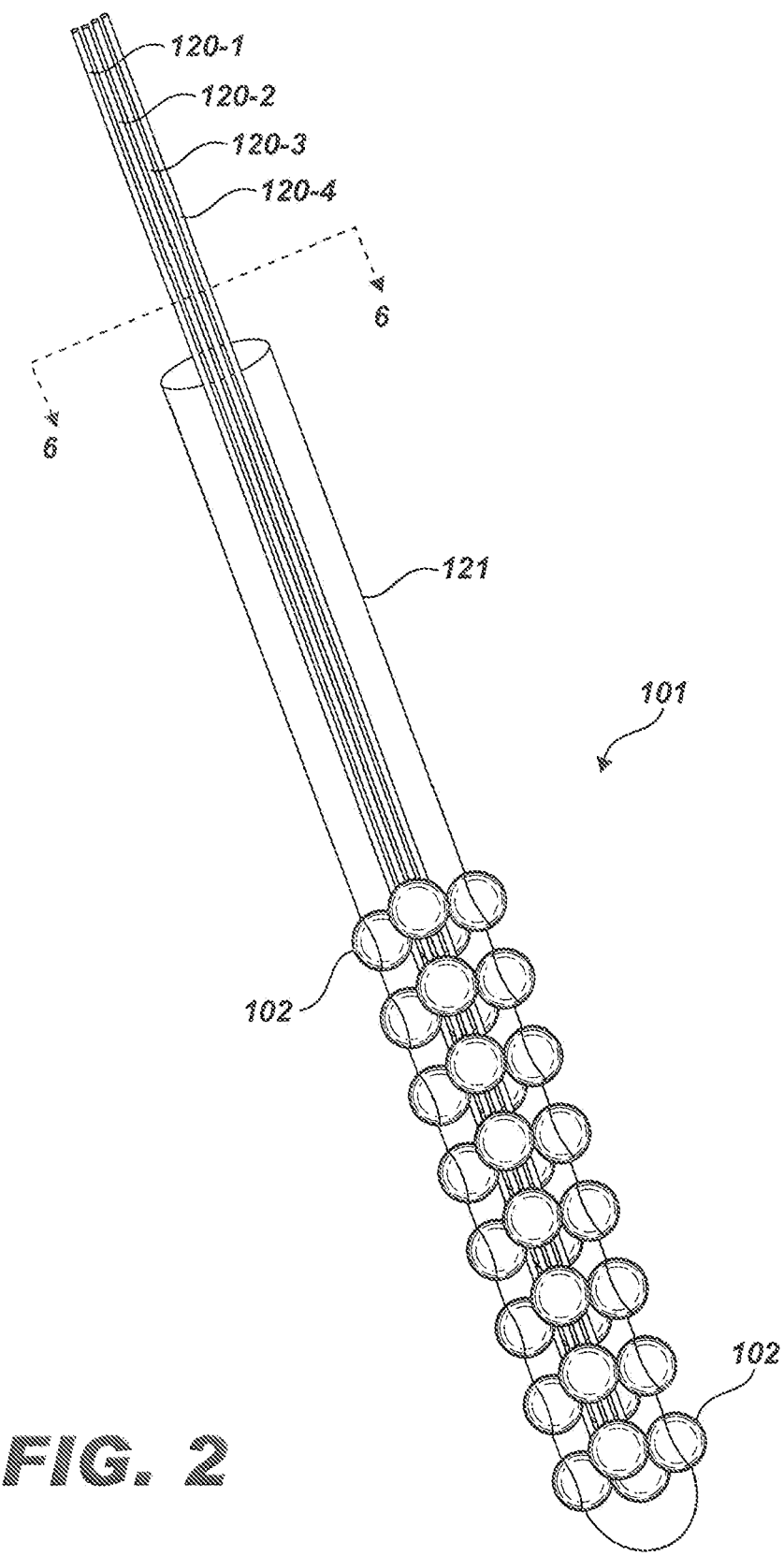
FIG. 2 illustrates an exemplary lead assembly according to principles described herein.

An exemplary lead assembly 101 is illustrated in FIG. 2. As shown in FIG. 2, the lead assembly 101 may include a plurality of electrode assemblies 102 disposed thereon. In some examples, as shown in FIG. 2, the electrode assemblies 102 are arranged in a multi-dimensional configuration. As will be described in more detail below, one or more of the electrode assemblies 102 may include one or more active switching elements to facilitate stimulation via a selectable subset of the electrode assemblies 102. In this manner, any type of stimulation (e.g., linear or radial stimulation) may be applied to one or more stimulation sites within a patient.

The electrode assemblies 102 may have any shape and/or dimension as may serve a particular application. For example, as shown in FIG. 2, one or more of the electrode assemblies 102 may be spherical. Additionally or alternatively, one or more of the electrode assemblies 102 may be cubic and/or of any other shape and/or dimension.

As shown in FIG. 2, the lead assembly 101 also includes a plurality of conductor wires 120 embedded within a lead body 121. Each of the wires 120 may be made out of any suitable conductive material (e.g., platinum, titanium or stainless steel) and may be individually insulated. The lead body 121 may be made out of a polymer material such as, but not limited to, silicone, polyurethane, or polytetrafluoroethylene (PTFE). The lead body 121 may alternatively be made out of any other type of material as may serve a particular application.

The wires 120 are configured to facilitate electrical connection between the electrode assemblies 102 and electrical circuitry within the stimulator 100. In some examples, as will be described in more detail below, each of the wires 120 is coupled to a plurality of electrode assemblies 102 via a number of switching networks. In this manner, as will be described in more detail below, the number of wires 120 that has to be included within the lead assembly 101 may be minimized.

In some examples, each wire 120 may be dedicated to a unique function. For example, as shown in FIG. 2, the wires may include a first wire 120-1 dedicated to cathodic (−) stimulation or sensing, a second wire 120-2 dedicated to anodic (+) stimulation or sensing, a third wire 120-3 dedicated to providing a reference voltage (e.g., ground), and a fourth wire 120-4 dedicated to providing input/output settings (e.g., power signals, stimulation parameters, sensing parameters, and/or address identification. It will be recognized that wires dedicated to additional or alternative functions may additionally or alternatively be included within the lead assembly 101.

Figure 3:
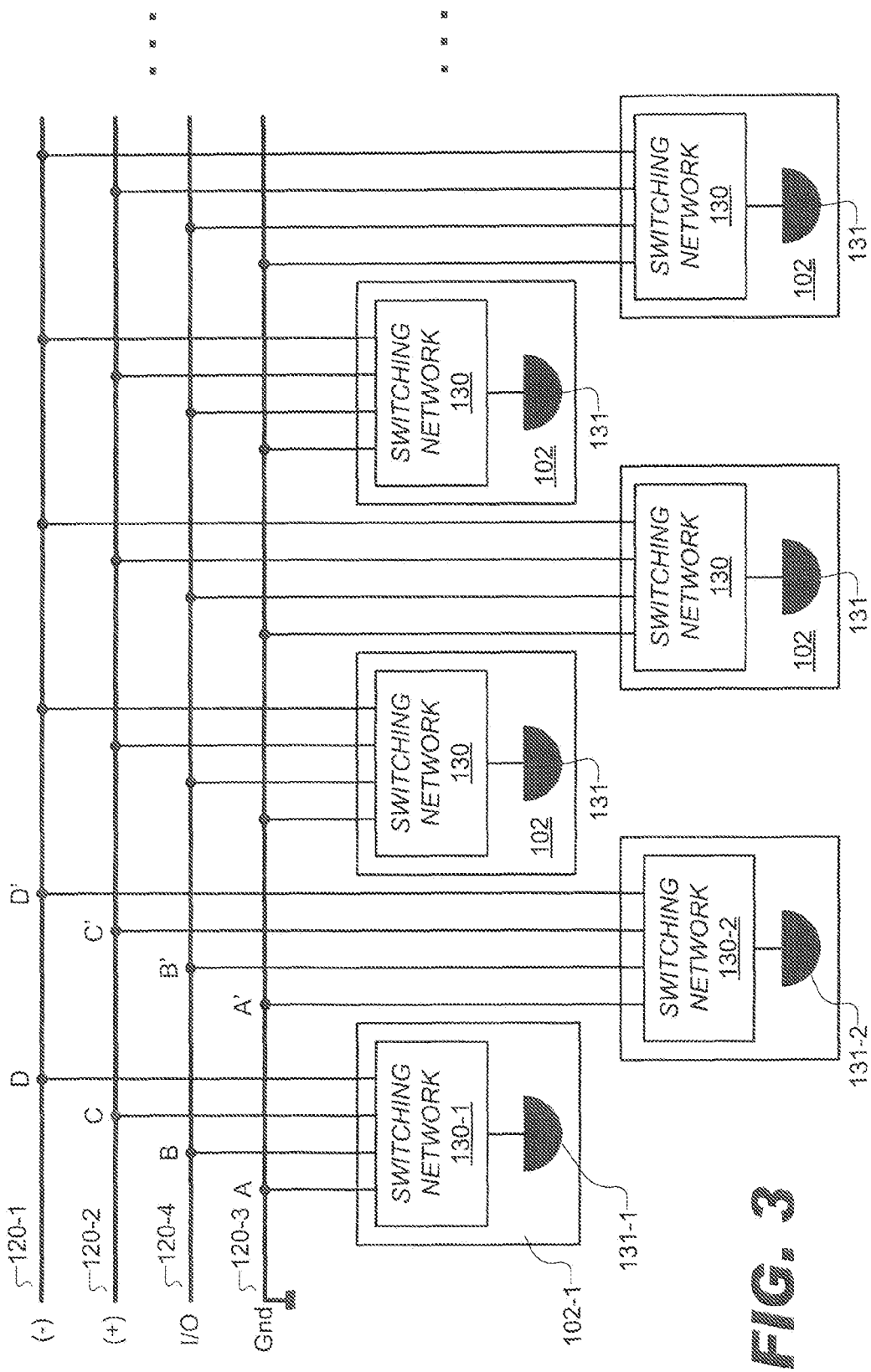
FIG. 3 illustrates an exemplary configuration wherein a plurality of electrode assemblies are coupled in parallel to the conductor wires via a plurality of switching networks according to principles described herein.

FIG. 3 illustrates an exemplary configuration wherein a plurality of electrode assemblies 102 are coupled in parallel to the conductor wires 120 via a plurality of switching networks 130. In this manner, as will be described in more detail below, a single set of conductor wires 120 may be used to control the operation of each of a plurality of electrode assemblies 102.

As shown in FIG. 3, each electrode assembly 102 may include a switching network 130 and an electrode contact 131. The electrode contacts 131 may be made from any suitable conductive material including, but not limited to, platinum, iridium, tantalum, titanium, titanium nitride, niobium, stainless steel, or alloys of any of these. Each switching network 130, as will be described in more detail below, may include one or more components configured to control the stimulation that is applied via its corresponding electrode contact 131.

As shown in FIG. 3, each switching network 130 may be electrically coupled to each of the wires 120. For example, switching network 130-1 is coupled to the ground wire 120-3 at node A, the I/O wire 120-4 at node B, the anode wire 120-2 at node C, and the cathode wire 120-1 at node D. Likewise, switching network 130-2 is coupled to the ground wire 120-3 at node A', the I/O wire 120-4 at node B', the anode wire 120-2 at node C', and the cathode wire 120-1 at node D'. The remaining switching networks 130 within the lead assembly 101 may be coupled to the wires 120 in a similar manner.

Figure 4:
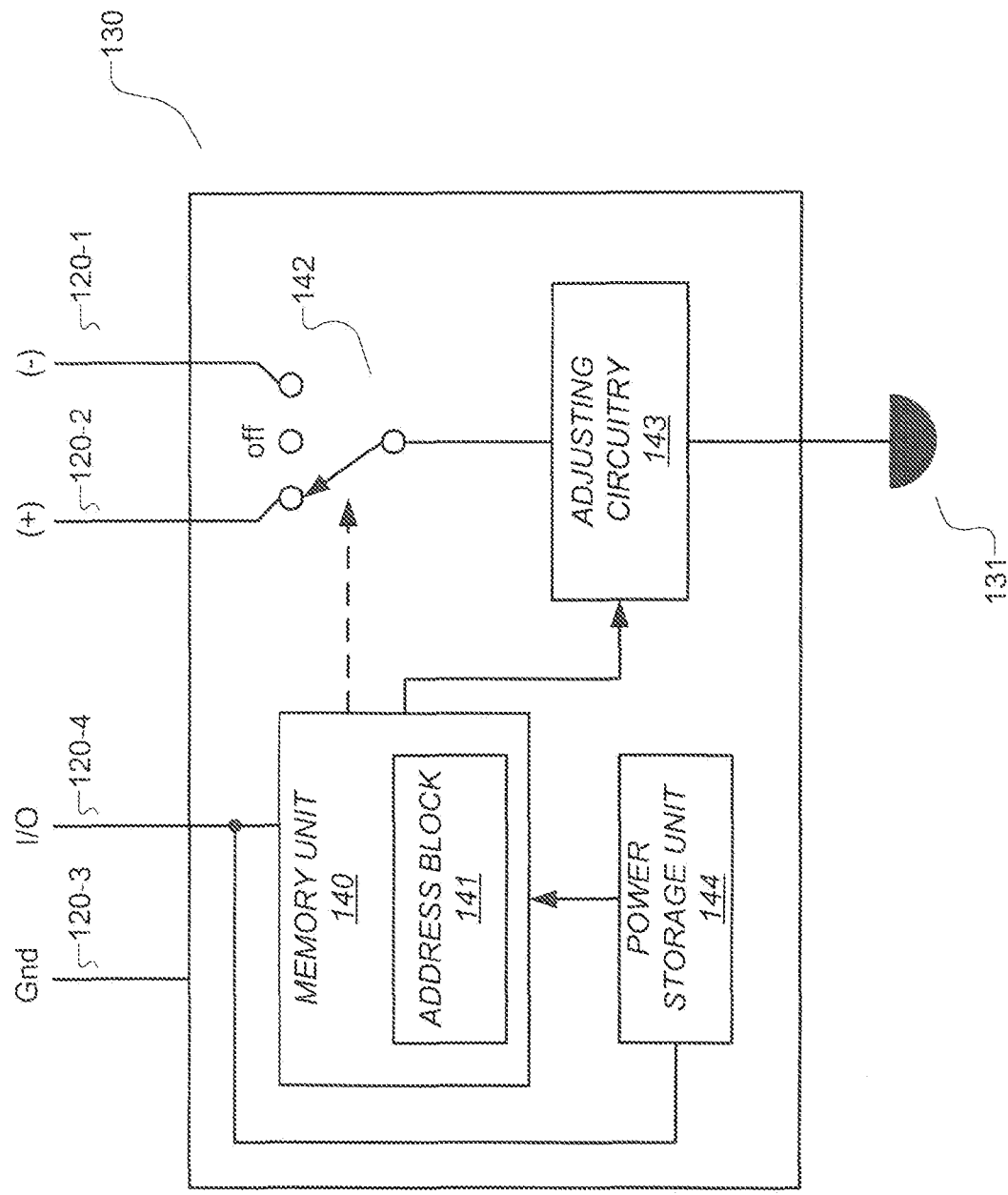
FIG. 4 illustrates an exemplary switching network according to principles described herein.

FIG. 4 illustrates an exemplary switching network 130 that may be used in connection with the systems and methods described herein. As shown in FIG. 4, the switching network 130 is electrically coupled to an electrode contact 131 and to each of the conductor wires 120.

In some examples, the switching network 130 may include an a memory unit 140, an address block 141, a switching element 142, adjusting circuitry 143 configured to adjust the stimulation current applied via the electrode contact 131, and a power storage unit 144 configured to receive and store power for one or more of the components within the switching network 130, it will be recognized that the components shown in FIG. 4 are merely exemplary and that additional or alternative components may be included within the switching network 130 as may serve a particular application. For example, one or more processors may additionally or alternatively be included within the switching network 130.

The memory unit 140 may include one or more registers, for example, and/or any other component configured to store one or more stimulation parameters and/or other control codes. In this manner, stimulation parameters (e.g., stimulation amplitude and/or frequency adjustments) and/or other control codes may be transmitted to the switching network 130 via the I/O wire 120-4 whereupon they are stored within the memory unit 140 and used to control the operation of the electrode contact 131.

In some examples, a portion of the memory unit 140 may be designated as an address block 141. The address block 141 may include one or more buffers and/or registers, for example, and may be configured to store a unique address or identification code that may be used to facilitate independent control or activation of the electrode contact 131.

Switching element 142 is configured to selectively couple the electrode contact 131 to the anode wire 120-2 or the cathode wire 120-1 in accordance with prescribed stimulation parameters. In this manner, the polarity of the electrode contact 131 may be selectively changed as may serve a particular stimulation strategy. The switching element 142 may include any combination of analog and/or digital circuitry as may serve a particular application. In some examples, as shown in FIG. 4, the switching element 142 may disable or turn "off" the electrode contact 131 by switching to an "off" position.

Adjusting circuitry 143 may include any suitable combination of components configured to adjust the stimulation current that is applied via the electrode contact 131. For example, the adjusting circuitry 143 may be configured to adjust the amplitude, frequency, and/or any other parameter of the stimulation current that is applied via the electrode contact 131. To this end, the adjusting circuitry 143 may include a digital-to-analog converter, one or more attenuators, one or more amplifiers, and/or any other circuitry configured to adjust the stimulation current.

Hence, the switching networks 130 described herein facilitate individual control of each electrode contact 131 that is a part of the lead assembly 101. For example, to control the operation of a particular electrode contact 131, the stimulator 100 may transmit one or more stimulation parameters accompanied by an address code of the electrode contact's corresponding switching network 130. The switching network 130 recognizes the address code and causes the electrode contact 131 to operate in accordance within the stimulation parameters. In this manner, different stimulation schemes may be implemented with a single set of conductor wires 120.

For example, monopolar and/or multipolar electrical stimulation may be generated and applied at a stimulation site via one or more of the electrodes contact 131 that are coupled to the conductor wires 120 via the switching networks 130. Monopolar stimulation is achieved by placing an electrode contact 131 acting as a cathode (or anode) adjacent to or near a stimulation site, and placing an electrode of opposite polarity relatively "far away" from the stimulation site. Bipolar stimulation is achieved by placing an anode-cathode pair adjacent to or near a stimulation site. Tripolar stimulation is achieved by placing a cathode surrounded by two anodes or an anode surrounded by two cathodes adjacent to or near a stimulation site. It will be recognized that monopolar and multipolar stimulation are merely illustrative of the many different stimulation schemes that may be used in connection with the systems and methods described herein.

In some examples, each switching network 130 may be protected with its own enclosure, which may be hermetic in some examples. An exemplary fabrication method that may be used to construct the enclosure of the switching network 130 is described in U.S. Pat. No. 6,826,430, incorporated herein by reference in its entirety. The enclosure may be made out of any suitable biocompatible material, e.g., silicone or polyurethane.

Figure 5:
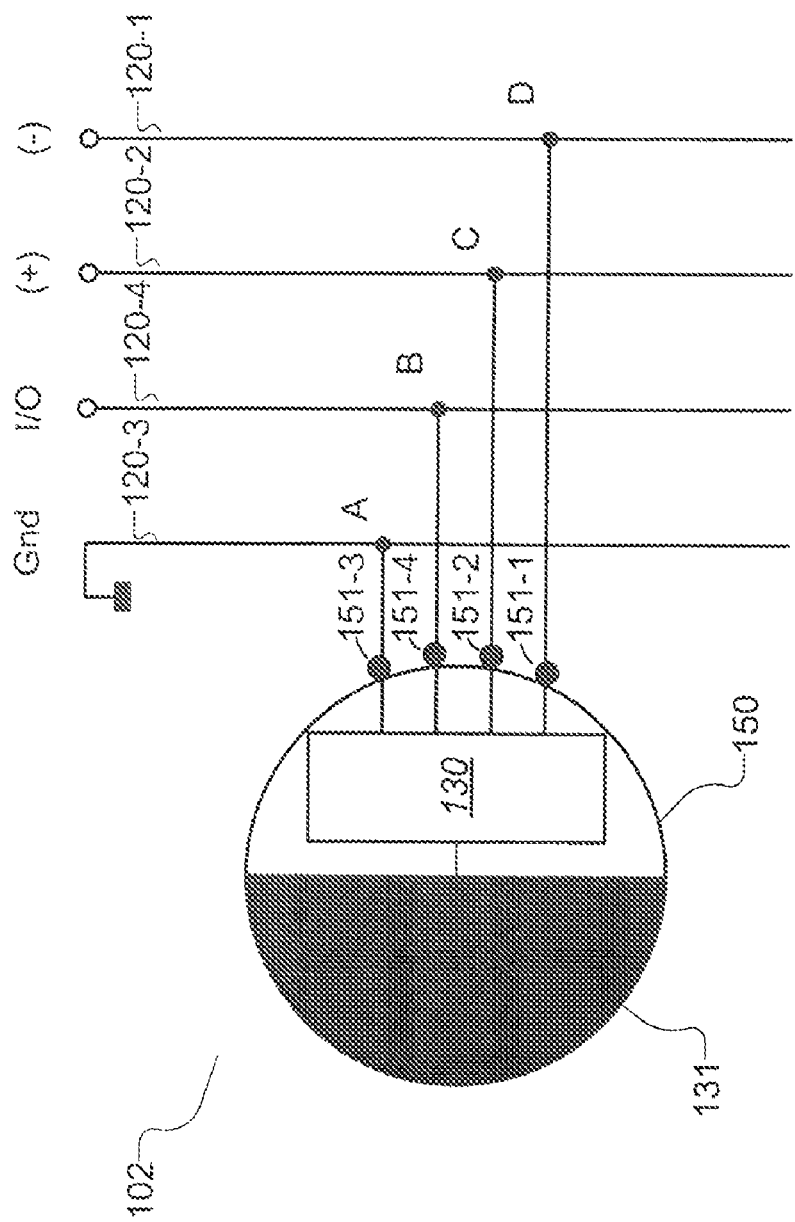
FIG. 5 illustrates en exemplary electrode assembly according to principles described herein.

For example, FIG. 5 illustrates an exemplary electrode assembly 102 wherein a switching network 130 is housed within an enclosure 150. As shown in FIG. 5, the switching network enclosure 150 may be hemispherically shaped and coupled to a corresponding hemispherically shaped electrode contact 131. Hence, the electrode contact 131 and switching network enclosure 150 together form a spherical electrode assembly 102. It will be recognized that the electrode contact 131 and/or switching network enclosure 150 may each have any other shape as may serve a particular application. For example, as will be described in more detail below, the electrode contact 131 and/or switching network enclosure 150 may be cubic.

Also shown in FIG. 5 are a number of ball connectors 151-1 through 151-4, collectively referred to as 151, in some examples, the ball connectors 151 provide electrical connection between each of the conductor wires 120 and the switching network 130. For example, ball connector 151-1 may be electrically coupled to conductor wire 120-1, ball connector 151-2 may be electrically coupled to conductor wire 120-2, etc. Each ball connector 151 may be made out of any suitable conductive material such as, but not limited to, platinum, iridium, tantalum, titanium, titanium nitride, niobium, stainless steel, or alloys of any of these.

In some examples, the electrical connection between the ball connectors 151 and their corresponding conductor wires 120 may be facilitated through the use of one or more conductive wires, conductive epoxy, and/or any other conductive medium.

It will be recognized that the ball connectors 151 are merely illustrative of the many different structures that may be used to provide electrical connection between each of the conductor wires 120 and the switching network 130. For example, one or more conductive traces, conductive epoxy, wires, or the like may be used to provide electrical connection between each of the conductor wires 120 and the switching network 130. Moreover, as will be described in more detail below the ball connectors 151 may be used to facilitate interconnection between a plurality of connector assemblies 130.

As mentioned, the electrode assembly 102 shown in FIG. 5 may be hermetically sealed. Any suitable process may be used to make the electrode assembly 102 hermetic. For example, the internal components of the electrode assembly 102 may be located on a feedthrough-less silicone chip with a number (e.g., 4 or 5) exposed connections. The exposed connections may be in the form of the ball connectors (e.g., ball connectors 151). Alternatively, the exposed connectors may take any other shape or form.

Hermeticity may be achieved by coating the chip with a thin layer of parylene, and later depositing by reactive sputtering silicon nitride ($Si_3N_4$), silicon dioxide ($SiO_2$), and/or silicon oxinitride, exposing only the connection and later applying the medical grade silicone to isolate it after welding the wires to the contacts. The exposed connections may then be directly welded or otherwise connected to the feedthroughs of a neighboring electrode assembly 102 and/or connected by one or more conductive wires.

Figure 6:
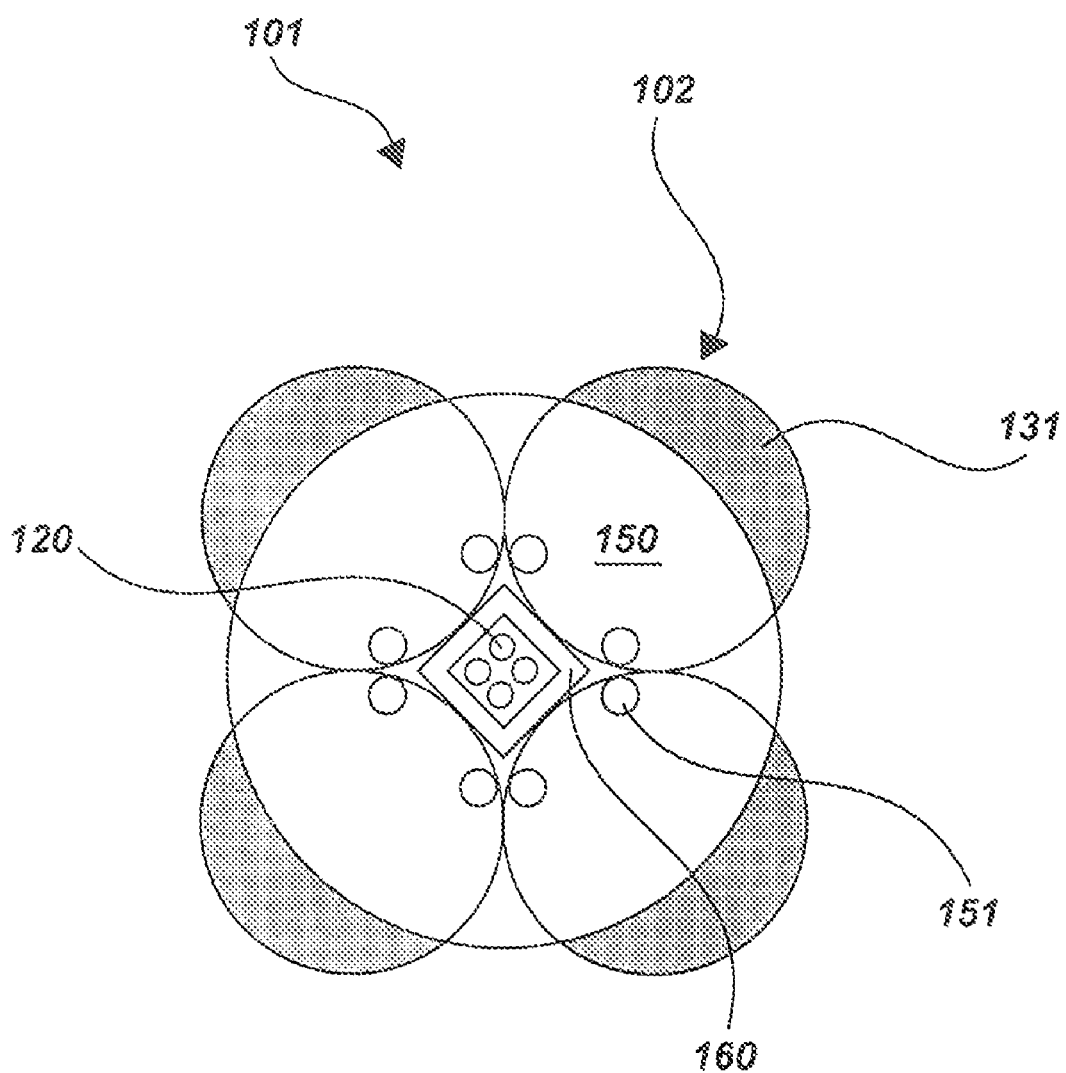
FIG. 6 is a cross-sectional top view of the lead assembly of FIG. 2 according to principles described herein.

FIG. 6 is a cross-sectional top view of the lead assembly 101 taken along the perspective line (2-2) indicated in FIG. 2. FIG. 6 shows four radially positioned electrode assemblies 102 for illustrative purposes only. It will be realized that the any number of electrode assemblies 102 may be included in any orientation as may serve a particular application.

As shown in FIG. 6, the lead assembly 101 may include a wire guide 160 extending at least partially therethrough through which the conductor wires 120 may pass. The wire guide 160 may be made out of any suitable material as may serve a particular application. In some examples, the wire guide 160 may be physically attached to one or more portions of the electrode assemblies 102.

As shown in FIG. 6, each of the electrode assemblies 102 includes one or more ball connectors 151. As described hereinabove, the ball connectors 151 may be used to facilitate electrical connection between each of the conductor wires 120 and the switching networks 130.

As shown in FIG. 6, at least a portion of each of the switching network enclosures 150 may be disposed within the lead assembly 101. Additionally or alternatively, at least a portion of each of the switching network enclosures 150 may be located external to the lead assembly 101 with the electrode contacts 131.

Figure 7:
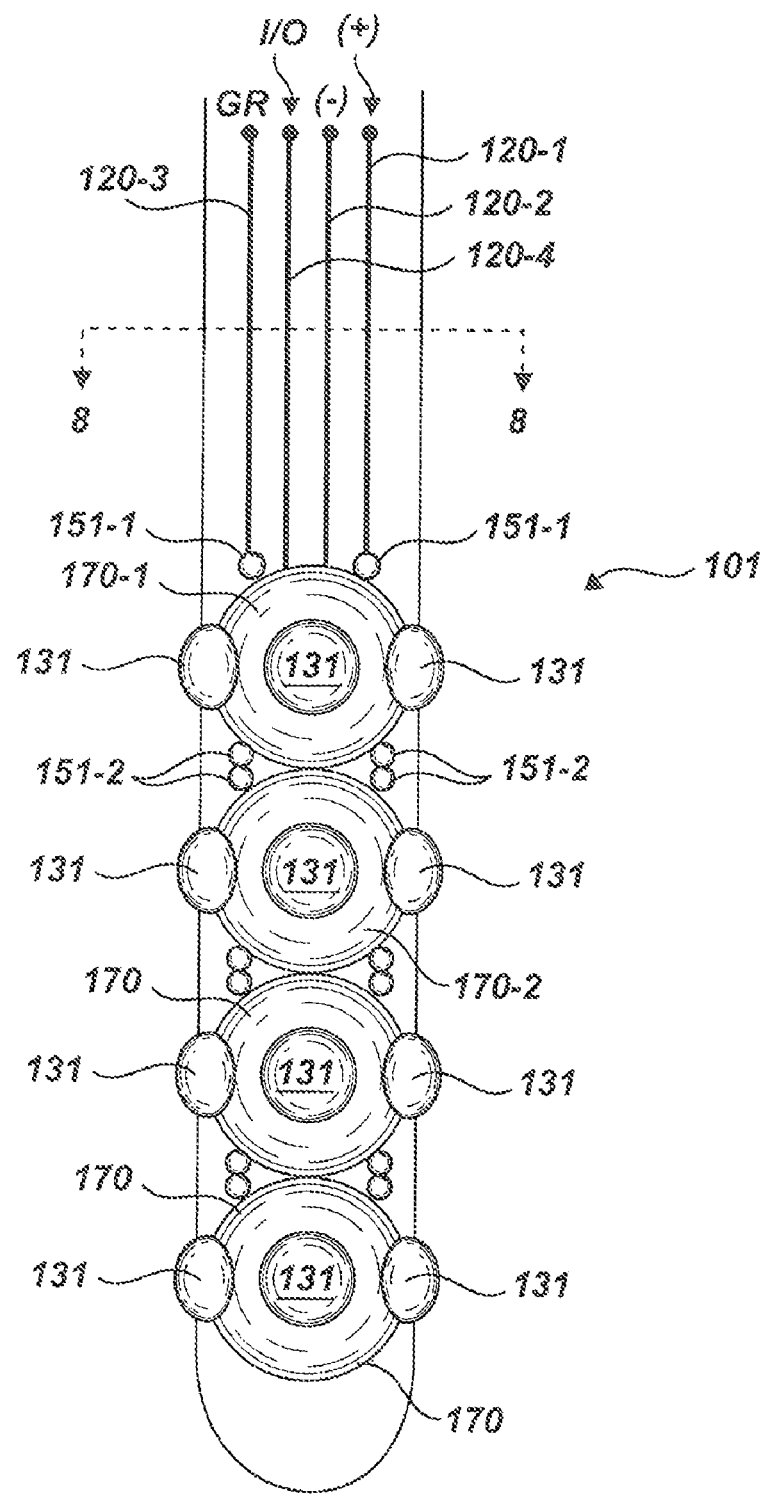
FIG. 7 illustrates an alternative configuration of the lead assembly according to principles described herein.
Figure 8:
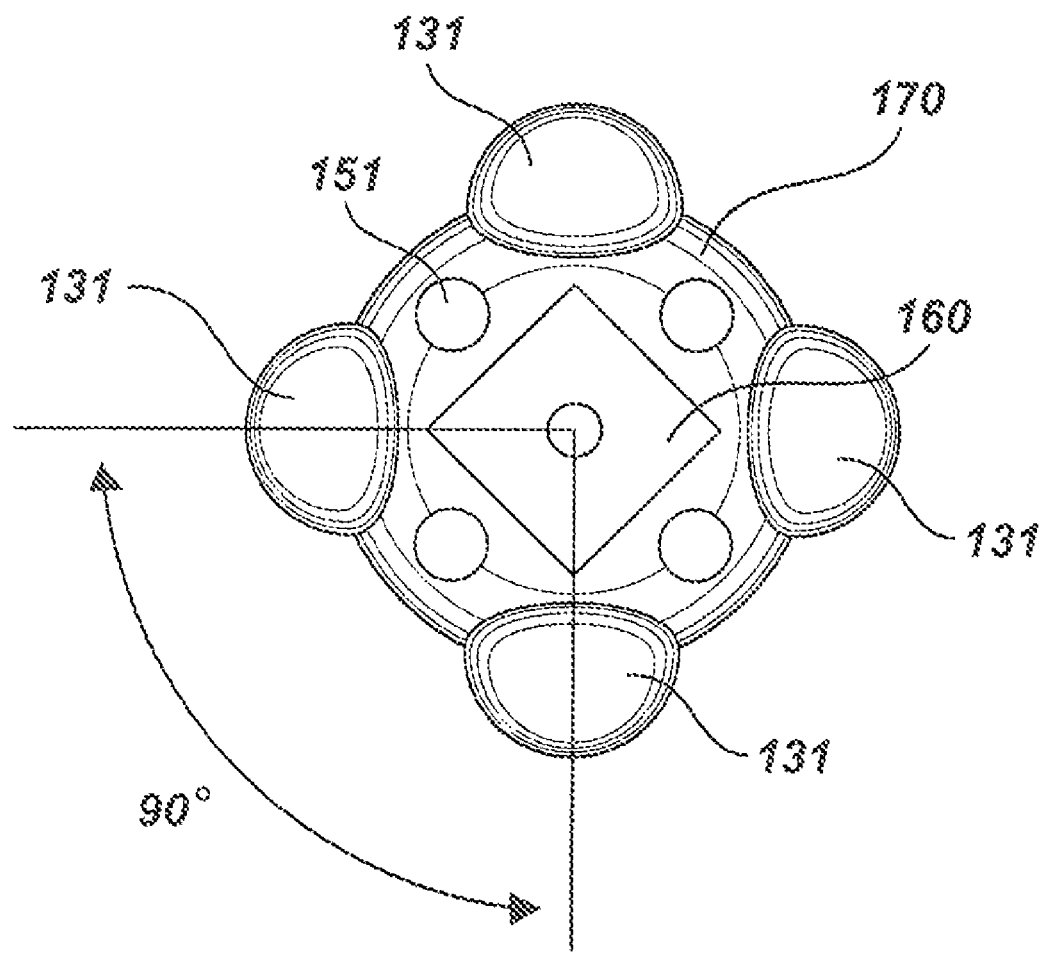
FIG. 8 is a cross-sectional top view of the lead assembly of FIG. 7 according to principles described herein.

FIG. 7 illustrates an alternative configuration of the lead assembly 101. FIG. 8 is a cross-sectional top view of the lead assembly 101 of FIG. 7 taken along the perspective line (8-8) shown in FIG. 7. As shown in FIGS. 7-8, a single enclosure 170 may be used to house the switching networks 130 corresponding to a plurality of electrode contacts 131. For example, the enclosure labeled 170-1 may be configured to house the switching networks 130 for four electrode contacts 131. It will be recognized that each enclosure 170 may be configured to house any number of switching networks 130 as may serve a particular application. Moreover, it will be recognized that each of the enclosures 170 may be hermetic.

In some alternative examples, a single switching network 130 may correspond to and control a plurality of electrode contacts 131. For example, the enclosure labeled 170-1 may be configured to house a single switching network 130 that is configured to control the operation of four electrode contacts 131.

In some examples, ball connectors 151 may be used to pass signals carried on conductor wires 120 through to each of the switching networks 130 within each of the enclosures 170. For example, as shown in FIG. 7, each conductor wire 120 may be electrically connected a first set of ball connectors 151-1. These ball connectors 151-1 are electrically coupled to each of the switching networks 130 that are located within the enclosure 170-1. One or more conductive vies located within the enclosure 170-1 may be provided to electrically couple the first set of bail connectors 151-1 to a second set of ball connectors 151-2. Bali connectors 151-2 in turn are electrically coupled to the switching networks 130 that are located within enclosure 170-2, in this manner, the conductor wires 120 may be electrically coupled to the switching networks 130 within each of the enclosures 170.

Figure 9:
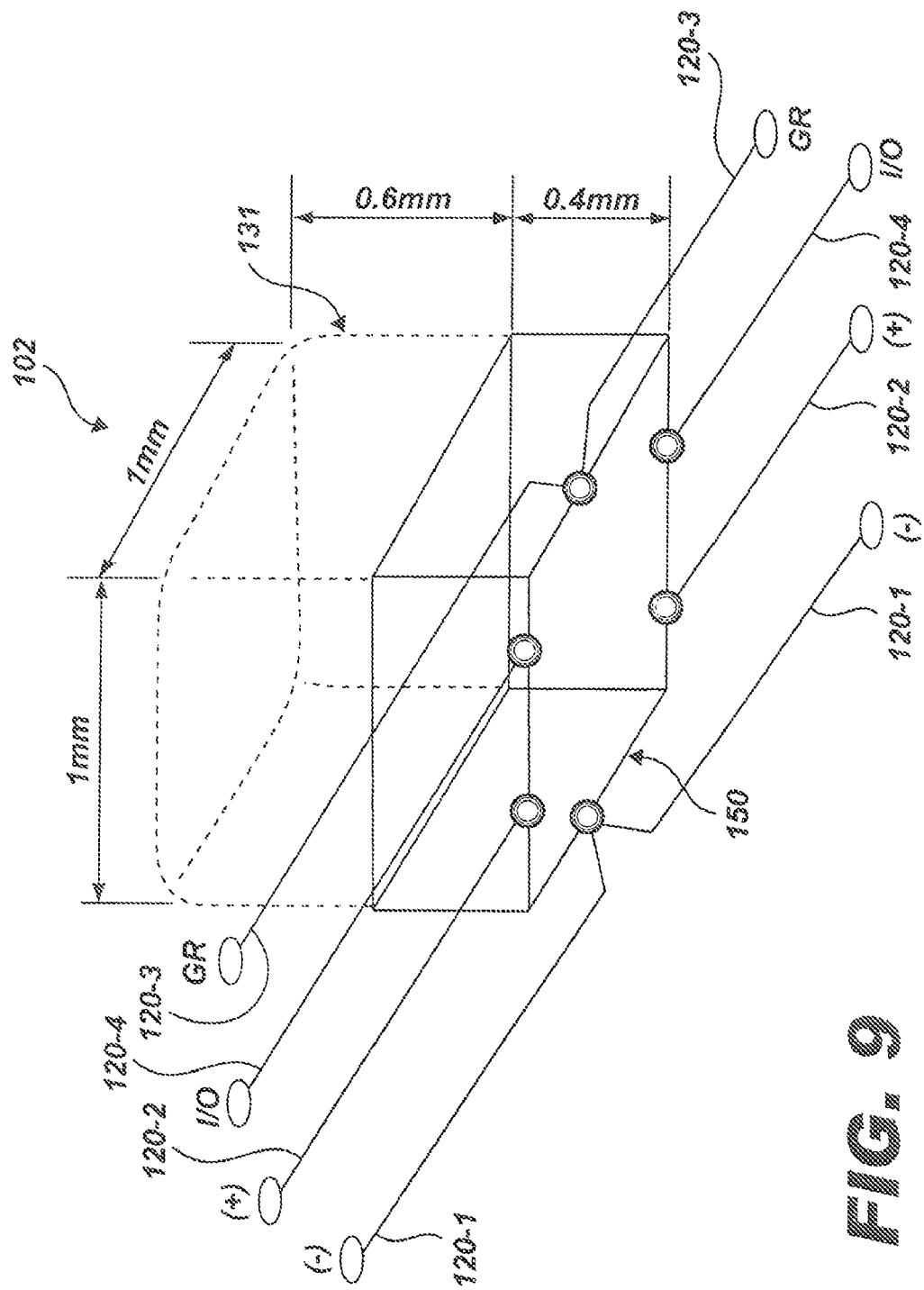
FIG. 9 illustrates an exemplary electrode assembly in the shape of a cube according to principles described herein.

As mentioned, the electrode assembly 102 may have any suitable shape. For example, FIG. 9 illustrates an exemplary electrode assembly 102 in the shape of a cube. As shown in FIG. 9, the cubic electrode assembly 102 includes a cubic switching network enclosure 150 coupled to a cubic electrode contact 102. The cubic enclosure 150 is configured to house a switching network 130 and may be hermetic in some examples.

The electrode contact 102 is illustrated by dashed lines in FIG. 9 for illustrative purposes. Exemplary dimensions of the cubic electrode contact 102 are given in FIG. 9 for illustrative purposes. However, it will be recognized that the electrode contact 102 may have any suitable dimension as may serve a particular application.

Figure 10:
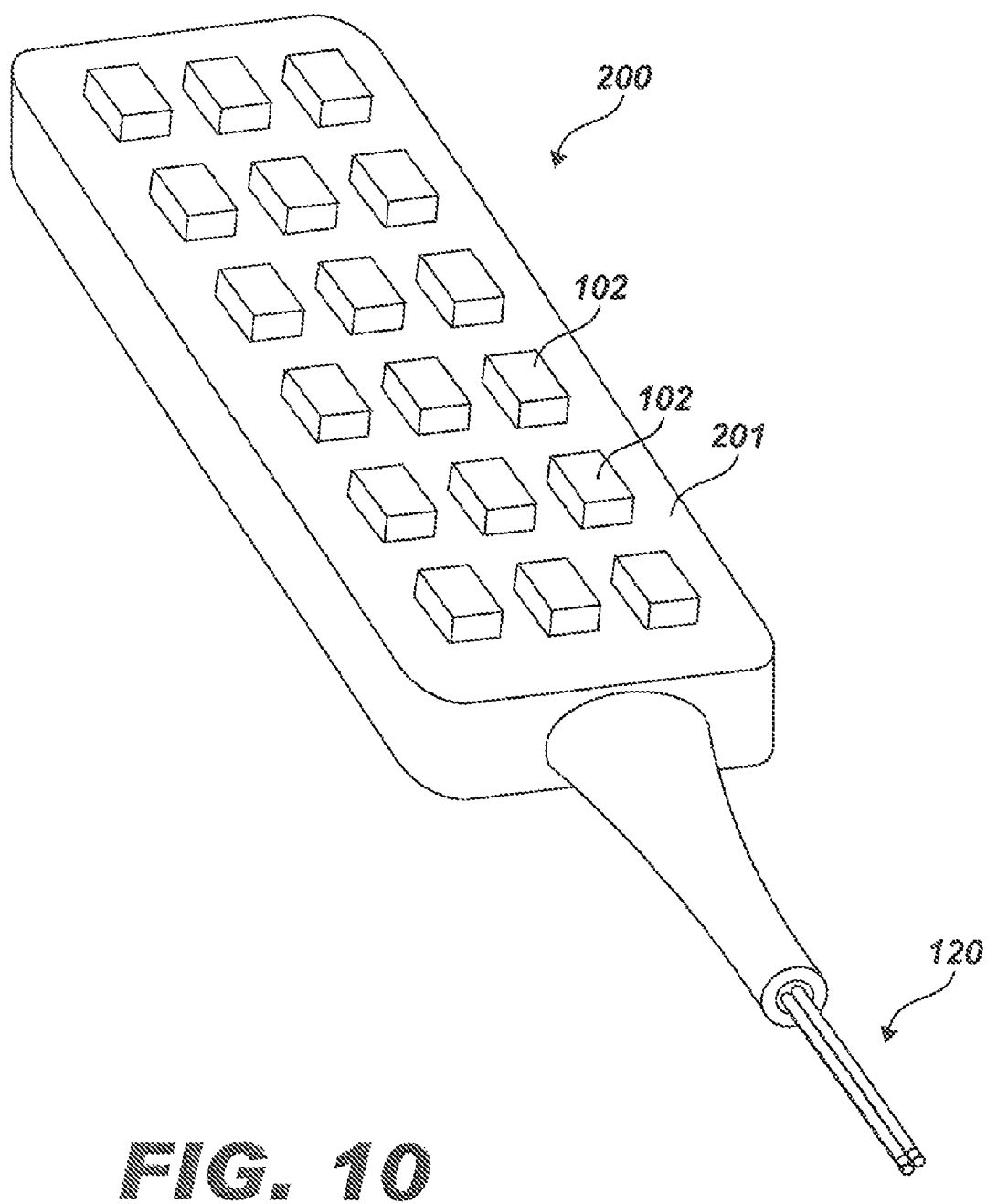
FIG. 10 illustrates an exemplary paddle lead assembly according to principles described herein.

FIG. 10 illustrates an exemplary paddle lead assembly 200 that may be used in connection with the systems and methods described herein. As shown in FIG. 10, a plurality of electrode assemblies 102 may be disposed on one or more surfaces 201 of the lead assembly 200. Each electrode assembly 102 is cubic for illustrative purposes only. Moreover, it will be recognized that the particular arrangement of electrode assemblies 102 may vary as may serve a particular application.

Figure 11:
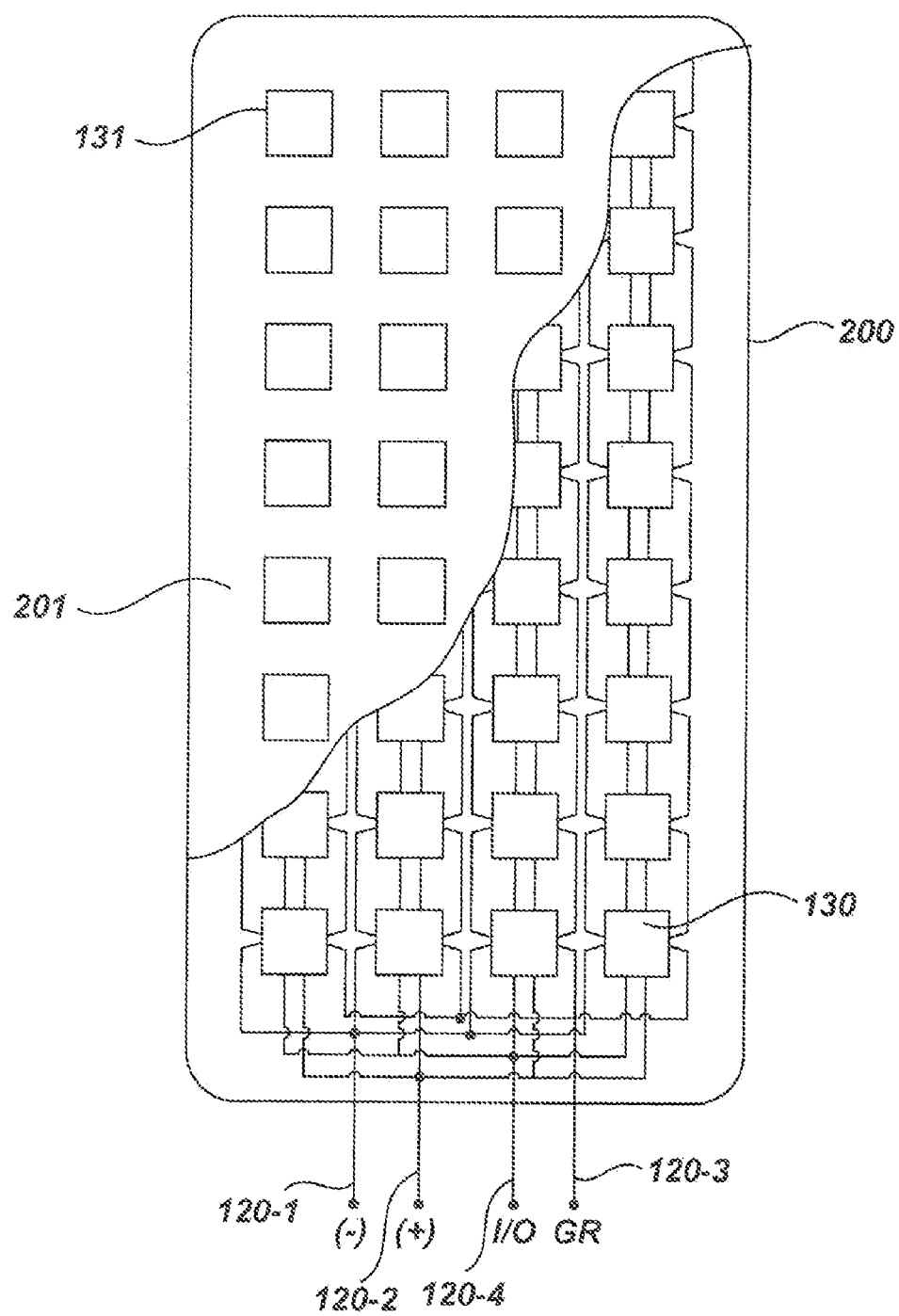
FIG. 11 is a cut-away depiction of the paddle lead assembly of FIG. 10 according to principles described herein.

The electrode assemblies 102 shown in FIG. 10 are each electrically coupled to each of the conductor wires 120 via a number of corresponding switching networks 130. FIG. 11 is a cut-away depiction of the paddle lead assembly 200 of FIG. 10 and shows a number of the switching networks 130 that are a part of the electrode assemblies 102. As shown in FIG. 11, each of the conductor wires 120 are electrically coupled to each of the switching networks 130. In this manner, the stimulation applied via each of the electrode contacts 131 may be individually controlled.

Hence, lead assemblies 101 described herein may be used to effectively deliver electrical stimulation to one or more targeted locations within a patient. Because the number of electrode assemblies 102 is not limited by the number of conductor wires 120, a lead assembly 101 as described herein may have more electrode assemblies 102 than traditional lead assemblies. In general, the lead assembly 101 may includes an n-by-m array of electrode assemblies 102. In this case, any combination of a corresponding n-by-m location area may be stimulated with the stimulator 100.

Figure 12:
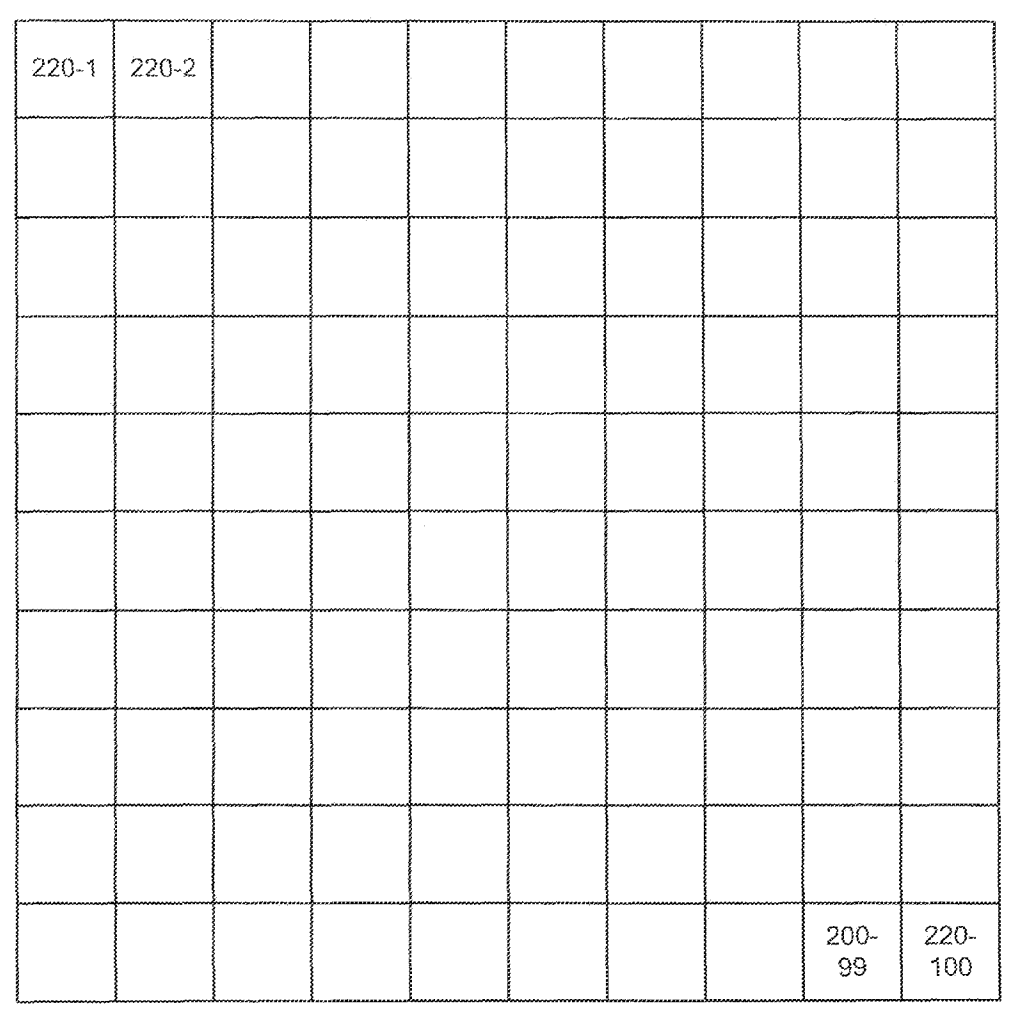

For example, FIG. 12 shows an exemplary ten-by-ten area (e.g., 220-1 through 220-100) within a patient that may be stimulated using a corresponding ten-by-ten array of electrode assemblies 102. To stimulate a particular location, e.g., 220-1, the stimulator 100 may selectively enable stimulation to be applied via the location's corresponding electrode assembly 102 by transmitting appropriate control codes to the electrode assembly's switching network 130. It will be recognized that any stimulation pattern may be used in accordance with any stimulation parameters as may serve a particular application.

The preceding description has been presented only to illustrate and describe embodiments of the invention. It is not intended to be exhaustive or to limit the invention to any precise form disclosed. Many modifications and variations are possible in light of the above teaching.

What is claimed is:
1. A lead assembly comprising:
 a lead body having a plurality of conductor wires embedded therein, wherein the plurality of conductor wires comprises an input/output wire, an anode wire, and a cathode wire, wherein the input/output wire, the anode wire, and the cathode wire are separate wires;
 a plurality of electrode contacts at least partially disposed on an outer surface of the lead body, wherein each of the electrode contacts is configured to apply stimulation current to one or more stimulation, sites; and
 a plurality of switching networks disposed in the lead body, each switching network corresponding to and config- ured to control an operation of one or more of the plurality of electrode contacts, wherein each of the switching networks comprises a memory unit coupled to the input/output wire and configured to store one or more unique address codes and one or more stimulation parameters configured to facilitate independent control of each of the electrode contacts, a switching element configured to couple and decouple at least one of the plurality of electrode contacts to the anode wire or the cathode wire in response to signals received at the memory unit from the input/output wire, and adjusting circuitry coupled to the switching element and the memory unit and configured to adjust one or more of the stimulation parameters;

wherein the input/output wire, the anode wire, and the cathode wire are electrically coupled to each of the switching networks.

2. The lead assembly of claim 1, wherein the plurality of conductor wires further comprises a ground wire that is separate from the input/output wire, the anode wire, and the cathode wire.

3. The lead assembly of claim 1, wherein each of the switching networks is further configured, to selectively switch between coupling a corresponding electrode contact to the anode wire, coupling the corresponding electrode to the cathode wire, or, in an off position, decoupling the corresponding electrode from both the anode wire and the cathode wire.

4. The lead assembly of claim 1, further comprising one or more hermetically sealed enclosures each configured to house one or more of the switching networks.

5. The lead assembly of claim 1, further comprising one or more ball connectors configured to electrically couple one or more of the conductor wires to one or more of the switching networks.

6. The lead assembly of claim 5, further comprising a square wire guide coupled to a portion of at least one of the ball connectors.

7. The lead assembly of claim 1, wherein each of the electrode contacts is cubic shaped, and wherein each of the switching networks is disposed within a cubic shaped enclosure and configured and arranged to couple to each of the electrode contacts to form a electrode assembly unit.

8. The lead assembly of claim 1, wherein the one or more stimulation parameters comprises stimulation amplitude.

9. The lead assembly of claim 1, wherein the one or more stimulation parameters comprises frequency adjustments.

10. The lead assembly of claim 1, wherein each of the electrode contacts is hemispherically shaped, and wherein each of the switching networks is disposed within a complementary hemispherically shaped enclosure and configured and arranged to couple to each of the electrode contacts to form a spherical electrode assembly unit.

11. The lead assembly of claim 1, wherein each switching network corresponds to and is configured to control the operation of exactly one of the plurality of electrode contacts.

12. The lead assembly of claim 1, wherein the adjusting circuitry comprises an element selected from an attenuator or an amplifier.

13. A system comprising:
animplantable stimulator configured to generate electrical stimulation current; and
the lead assembly of claim 1 coupleable to the implantable stimulator.

14. The system of claim 13, wherein the implantable stimulator is configured to selectively apply the stimulation current to one or more stimulation sites via a subset of the electrode contacts by transmitting one or more address codes corresponding to the subset of the electrode contacts to one or more of the switching networks via the input/output wire.

15. The system of claim 13, wherein each of the switching networks is further configured to selectively switch between coupling a corresponding electrode contact to the anode wire, coupling the corresponding electrode to the cathode wire, or, in an off position, decoupling the corresponding electrode from both the anode wire and the cathode wire.

16. The system of claim 13, further comprising one or more hermetically sealed enclosures each configured to house one or more of the switching networks.

17. The system of claim 13, further comprising one or more ball connectors configured to electrically couple one or more of the conductor wires to one or, more of the switching networks.

18. A method comprising:
generating electrical stimulation current;
providing a lead body having a plurality of conductor wires embedded therein, wherein the plurality of conductor wires comprises an input/output wire an anode wire, and a cathode wire, wherein the input/output wire, the anode wire, and the cathode wire are separate wires, the lead body further comprising a plurality of electrode contacts coupled to the plurality of conductor wires, each electrode contact having a corresponding switching network configured to control an operation thereof, wherein the input/output wire, the anode wire, and the cathode wire are electrically coupled to each of the switching networks, each of the switching networks comprising a memory unit coupled to the input/output wire and configured to store one or more unique address codes and one or more stimulation parameters configured to facilitate independent control of each of the electrode contacts, a switching element configured to couple and decouple at least one of the plurality of electrode contacts to the anode wire or the cathode wire in response to signals received at the memory unit from the input/output wire, and adjusting circuitry coupled to the switching element and the memory unit and configured to adjust one or more of the stimulation parameters;

storing one or more unique address codes and one or more stimulation parameters within the memory unit of each of the switching networks for facilitating independent control of each of the electrode contacts; and selectively applying the stimulation current to one or more stimulation sites via a subset of the electrode contacts by transmitting one or more stimulation parameters to one or more of the switching networks via one or more of the conductor wires.

19. The method of claim 18, further comprising adjusting the stimulation current applied via the subset of the electrode contacts with the adjusting circuitry of one or more of the switching networks.

20. The method of claim 18, wherein the method further comprises selectively coupling one or more of the electrode contacts to the anode wire and coupling one or more of the electrode contacts to the cathode wire.

* * * * *